United States Patent [19]

Harrison et al.

[11] Patent Number: 5,307,052
[45] Date of Patent: Apr. 26, 1994

[54] BIO-AMPLIFIER FOR SENSING THE BIO-ELECTRIC FIELD OF FISH

[75] Inventors: Frank P. Harrison, Alum Ridge; David Gruber, Christiansburg, both of Va.

[73] Assignee: Biological Monitoring, Inc., Blackburg, Va.

[21] Appl. No.: 871,741

[22] Filed: Apr. 21, 1992

Related U.S. Application Data

[63] Continuation-in-part of Ser. No. 611,664, Nov. 13, 1990, abandoned.

[51] Int. Cl.⁵ ............................................. G08B 23/00
[52] U.S. Cl. .................................... 340/573; 119/215
[58] Field of Search ............... 340/573, 753, 754, 762, 340/782; 364/413.03, 413.05; 328/740; 119/2, 3, 4

[56] References Cited

U.S. PATENT DOCUMENTS

| | | | |
|---|---|---|---|
| 3,450,990 | 6/1969 | Green | 324/76.39 |
| 3,958,235 | 5/1976 | Duffy | 340/782 |
| 4,723,511 | 2/1988 | Solman | 119/3 |

Primary Examiner—Hezron E. Williams
Assistant Examiner—Christine K. Oda

[57] ABSTRACT

The present invention provides a bio-amplifier in a water quality system. The bio-amplifier detects and amplifies a ventilatory behavior of a fish. The ventilatory behavior is converted to a signal. The signal is an instantaneous determination of the quality of water being tested.

3 Claims, 1 Drawing Sheet

BIO-AMPLIFIER FOR SENSING THE BIO-ELECTRIC FIELD OF FISH

This is a continuation-in-part application of U.S. Ser. No. 07/611,664, abandoned, filed Nov. 13, 1990, entitled "Bio-Amplifier for Sensing the Ventilatory Frequency of Fish".

BACKGROUND OF THE INVENTION

The present invention is directed to a bio-amplifier card provided for each fish in a system, including a Bio-Amp ® (manufactured by Biological Monitoring, Inc. (BMI)). The bio-amplifier card, upon detecting a bio-electrical field (generated by neuromuscular activity such as breathing) of fish, amplifies the signal for use in, for example, a water quality monitoring system. The fish are used as biological sensors. The system in which the bio-amplifier card is employed is described in U.S. Ser. No. 07/611,653, filed Nov. 13, 1990, now U.S. Pat. No. 5,140,855 to David Gruber, incorporated by reference herein.

The ventilatory behavior of fish has been used as an indicator of a toxic environment. Prior art systems are large, cumbersome and not particularly accurate. A large amount of data is required to be taken and analyzed over a period of time. Therefore, an alarm indicating that the water is contaminated is not instantaneous; rather, an extended period of time is necessary to make a contamination determination. It is necessary to develop a system which is efficient, accurate and capable of making a contamination determination in as short a time as possible.

SUMMARY OF THE INVENTION

It is an object of the present invention to provide a bio-amplifier in a water quality monitoring system which receives and amplifies a bio-electrical field generated by the ventilatory behavior or other locomotor behaviors of a fish.

It is another object of the present invention to provide a bio-amplifier which amplifies the bio-electrical signals generated by a fish's bio-electrical field, attenuates electrical signals caused by the fish's body motion except those generated by the mouth and gills during a breathing cycle and certain other locomotor behaviors, and displays an amplified instantaneous voltage which is output from each "bio-amplifier card" of the Bio-Amp ®, due to the fish's bio-electric field, on a display symmetrical about ground.

These objects are obtained by providing an amplifier which receives and amplifies the bio-electrical signals generated by the breathing of a fish and displays the amplified signals.

These objects, together with other objects and advantages which will be hereinafter subsequently apparent, reside in the details of construction and operation as more fully described and claimed, reference being had to the accompanying drawings forming a part hereof, wherein like reference numerals refer to like parts throughout.

DRAWINGS

FIG. 1 is a block diagram of a bio-amplifier according to the present invention; and FIG. 2 is a diagram of a display which is symmetrical about ground according to the present invention.

DESCRIPTION OF THE PREFERRED EMBODIMENT

Figure 1:
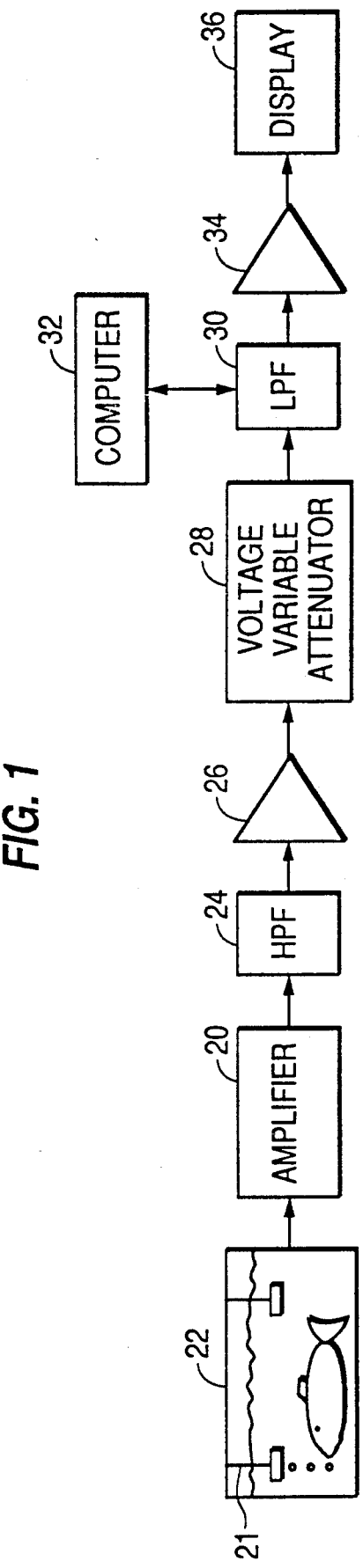
Figure 2:
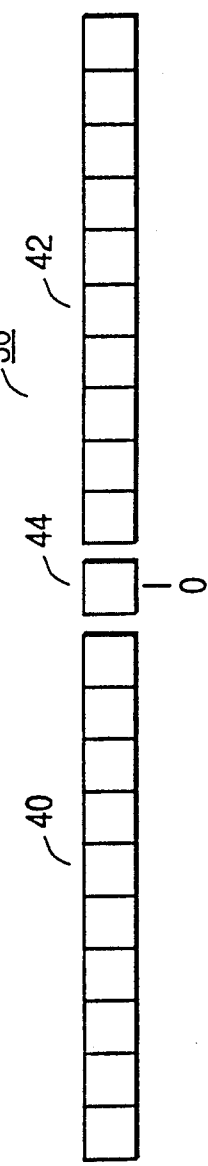

FIG. 1 is a block diagram of a bio-amplifier according to the present invention. The entire system of the present invention is set forth in U.S. Pat. No. 5,140,855, which is incorporated by reference herein, as noted above. Before going into a detailed explanation of FIG. 1, a brief overview of the bio-amplifier will be given.

As a fish ventilates, the sum of its neuromuscular activities generates bio-electrical signals generated by neuromuscular activities such as heartbeat, and mouth and gill movement during breathing. The strongest of these signals is the ventilatory signal. This signal is a microvolt signal and is not strong enough to be detected without amplification. The ventilatory signal is picked up by electrodes 21 in a Bio-Sensor ® (manufactured by Biological Monitoring, Inc. (BMI) and disclosed in U.S. patent application having Ser. No. 07/611,744, filed on Nov. 13, 1990, to Gradzki et al., and incorporated by reference herein) and input to a bio-amplifier 20 (Bio-Amp ®, manufactured by Biological Monitoring, Inc.) which amplifies the signals and filters out unwanted noise to make it usable to a computer. The filtered signal is input to a computer 32 where an analog-to-digital (A/D) converter converts the signal to digital form. This signal may then be displayed on the computer's monitor screen if the proper hardware and software are provided, or on an LED display 36 and output for interfacing with the computers and/or strip chart recorders on a real time basis. It should be noted that the signal is conditioned proportionally for the LED display 36.

In FIG. 1, a low-noise instrumentation amplifier 20 is used to pick up bio-electrical signals caused by a fish's 22 breathing (ventilatory signal). The bio-electrical signals are then input to a 0.1 Hz high-pass filter 24, which attenuates the interference caused by the fish's body motions which are also picked up by the instrumentation amplifier 20. The high-pass filter 24 is set at 0.1 Hz for attenuating the fish's body motions, while maintaining the signals corresponding to the fish's breathing. A first gain amplifier 26 is provided to increase the gain on the output of the high-pass filter 24. A voltage variable attenuator 28 receives the output from the first gain amplifier 26. The voltage variable attenuator 28 is also connected to a potentiometer (not shown) for manual gain control. A voltage tunable low-pass 6-pole Butterworth type filter 30 then receives the filtered amplified signal. The low-pass 6-pole Butterworth type filter 30 has an upper cut-off frequency which is controlled by a computer 32. The amplifier 20, high-pass filter 24 and low-pass filter 30 are used to process bio-electric field signals generated by each fish.

The low-pass 6-pole Butterworth type filter 30 is used because the computer 32 which controls the cut-off frequency of the low-pass 6-pole Butterworth type filter 30 digitizes the bio-electric signal in an analog-to-digital (A/D) converter (not shown). The A/D conversion sampling rate imposes a limitation on the highest frequency signal, which is slightly less than one-half the sampling rate. Therefore, energy input to the A/D converter which is more than one-half the sampling rate creates interference. The low-pass 6-pole Butterworth filter 30 does not allow energy at frequencies higher than one-half the sampling rate into the A/D converter, thereby preventing the interference. The Butterworth filter 30 is tunable so that it can be set according to desired functions of the system.

A second gain amplifier 34 is provided at the output of the 6-pole Butterworth type filter 30. The output of the second gain amplifier 34 is then input to a 20-segment LED amplitude display 36 which displays the amplified instantaneous voltage corresponding to the fish's 22 breathing.

The above-described circuits, e.g., the amplifiers and filters, can be any typical devices which provide the characteristics (e.g., cut off frequencies, etc.) which are desired of the system.

In the LED display 36 different colored LEDs are provided. That is, if only a green zero LED is lit, the fish may be dead or producing a weak signal. In this case, for example, the operator would first increase the gain control. If again only the zero light remains on, the fish may be dead. Only then would the fish be directly observed so as not to disturb the other fish and cause them to breath erratically. If the signal is too great, the operator is alerted by the illumination of red LEDS. At this time, the operator would reduce the gain because the signals are clipped at the high gain and not seen by the computer software for data analysis. When the signal is just right, only green LEDs are lit. As the signal approaches a level too great for the typical analog-to-digital computer converter ($\pm 10$ volts maximum), but is not too great, yellow LEDs are lit alerting the operator to stand by. The red LEDs light only when the signals are too great (greater than or equal to 10 volts) alerting the user to reduce the gain.

The 20-segment LED amplitude display 36 comprises two 10-segment display controllers 40 and 42 with an extra LED 44 between the two 10-segment display controllers 40 and 42. The extra LED 44 represents a 0 level so that the display 36 is symmetrical about ground. The display also indicates that the device is actually receiving power and is not off. The LED display 36 is symmetrical about ground. That is, the center of the display is "0" with the same number of LED's to the right and left, i.e., positive and negative voltages are reflected on the display. The amplified instantaneous voltage is output from the bio-amplifier 20 and is directed to two locations—an LED display 36 and an output for computers and/or strip chart recorders. The amplified instantaneous voltage is the voltage input to the Bio-Amp ® that is amplified by the bio-amplifier and is directly input to the LED display 36. The LED display 36 indicates the magnitude of the amplified voltage on a moment-by-moment basis (real time basis).

The extra LED 44 functions by sensing if any LED in the display is lit. If any LED in either of the 10-segment display controllers 40 and 42 is lit, the extra LED 44 is extinguished. When all the LED's in each 10-segment controller 40 and 42 are off, the LED 44 is lit. This is accomplished by sensing all the currents across a resistor (not shown) connected to each anode of each LED 44. That is, a resistor is in series with a common anode connection to all 20 LED's and a positive power supply (not shown). When any of the 10-segment displays 40 and 42 is lit, there is a voltage drop across the resistor. When all of the lights are normally extinguished, the voltage drops to OV. A comparator is used to sense that the voltage is OV and the LED 44 is lit.

The LED display 36 provides a direct indication of the bio-electrical signals emitted by the fish. That is, the bio-amplifier 20 receives input signals from a single fish housed in a small tank 22 fitted with the pair of electrodes 21. In the present invention, a number of individual fish, each in their own tank, are used. Thus, a bio-amplifier "card" is required for each fish. The bio-amplifier cards are placed in a module along with a power supply and input and output terminals. This entire system forms the Bio-Amp ®. Signals outputted from each bio-amplifier 20 are processed such that they primarily represent the ventilatory behavior (breathing) and certain other locomotor activities of a fish on a real time basis. The output signals are analog and vary in voltage and polarity as a fish breathes or performs certain movements. The bio-amplifier 20 converts the bio-electric field to a voltage variable by measuring the differences in microvolt voltages between the two electrodes 21 in each tank receiving the signals (bio-electric field) generated by a fish.

The output of the bio-amplifier 20 is analog, as above-mentioned, and is directed in two directions. The first output is for interfacing to strip chart recorders and/or computers. Typically, these signals may range in magnitude as much as from $+15$ to $-15$ volts, and more commonly from $+10$ to $-10$ volts depending on the strength of the original fish signal and/or the gain setting on each bio-amplifier 20. The gain setting is adjusted at a knob by the user/operator in a control panel (not shown).

The second output is directed to the LED display 36. The LED display 36 requires signal conditioning. The LED display 36 on each bio-amplifier card consists of a total of 11 LED's (two ten segment LEDs and a single LED). As the first output to the computer/strip chart recorder interfacing varies in voltage, the LED display 36 is illuminated in such a manner as to correspond to that voltage. At any given time if the voltage is, for example, OV, only the center-most LED is illuminated. If the voltage is, for example, $+10$ volts or greater (in a negative direction), only the bottom (or left-most) LEDs are lit. From the center zero LED, each LED represents a voltage change of 1 volt. Since a number of fish are used in a system for testing water, one fish may breathe less deeply or have a stronger bio-electric signal than another fish. The present invention allows the gain of each signal from each fish to be adjusted so that there are comparable signal levels on each LED display 36.

The Bio-Amp ® of the present invention can be built in a standard rack-mounted card cage with an arrangement such that each individual amplifier can be removed. One Bio-Amp ® is provided for each fish. In the present invention, the Bio-Amp ® does not look at signals above approximately 8 Hz. This level is based on the frequency of the signals derived from the fish's breathing. This level, however, can be changed depending on the type of system employed and the biological monitor involved.

As mentioned above, the Bio-Amp ® of the present invention receives bio-electrical signals, including ventilatory behavior, generated by the breathing of fish and other locomotor activities. These bio-electric signals are converted to varying voltage, amplified, filtered and interfaced to an A/D converter and are then displayed. The amplitude of these signals indicates the quality of the water being tested. This system of the present invention provides the advantage of combining signal processing and display in one small package.

The foregoing is considered as illustrative only of the principles of the invention. Further, since numerous modifications and changes will readily occur to those skilled in the art, it is not desired to limit the invention to the exact construction and applications shown and described, and accordingly, all suitable modifications and equivalents may be resorted to, falling within the scope of the invention and the appended claims and their equivalents.

What is claimed is:

1. A bio-amplifier for use in a system which detects a bio-electric field generated by locomotor activities of fish and converts the bio-electric field into a varying voltage, and includes a computer and an A/D converter, comprising:
   an amplifier for receiving and amplifying bio-electrical signals from the bio-electric field generated by ventilatory activity of fish and outputting amplified bio-electrical signals;
   a high-pass filter, connected to said amplifier, for attenuating interference in said amplified bio-electrical signals and outputting a high-pass filtered signal;
   a low-pass filter, operatively connected to said high-pass filter and having a cut-off frequency determined by the computer, for preventing interference due to signals not created solely by the ventilatory and locomotor activities of the fish, said low-pass filter having a sampling frequency the same as a sampling frequency of the A/D converter;
   a voltage variable attenuator, operatively connected between said low-pass filter and said high-pass filter, for receiving the high-pass filtered signal and outputting a signal corresponding to the bio-electrical signals of fish to said low-pass filter; and
   a display, operatively connected to said low-pass filter, symmetrical about ground, for displaying an amplified instantaneous voltage signal corresponding to said low-pass filtered signal from said low-pass filter.

2. A bio-amplifier according to claim 1, wherein said low-pass filter comprises a voltage tunable low-pass 6-pole Butterworth type filter.

3. A bio-amplifier according to claim 2, wherein said display comprises:
   two 10-segment display controller means for displaying the amplified bio-electrical signals of the fish; and
   an extra LED in the middle of said two 10-segment LED display controller means as a zero point.

* * * * *